(12) United States Patent
Faller et al.

(10) Patent No.: US 7,387,774 B2
(45) Date of Patent: *Jun. 17, 2008

(54) METHOD OF ENHANCING FLUORIDATION AND MINERALIZATION OF TEETH

(75) Inventors: Robert Vincent Faller, Loveland, OH (US); Arif Ali Baig, Mason, OH (US); Donald James White, Jr., Fairfield, OH (US)

(73) Assignee: The Procter & Gamble Co., Cincinnati, OH (US)

( * ) Notice: Subject to any disclaimer, the term of this patent is extended or adjusted under 35 U.S.C. 154(b) by 248 days.

This patent is subject to a terminal disclaimer.

(21) Appl. No.: 10/734,381

(22) Filed: Dec. 12, 2003

(65) Prior Publication Data

US 2004/0126335 A1   Jul. 1, 2004

Related U.S. Application Data

(63) Continuation-in-part of application No. 10/319,108, filed on Dec. 13, 2002, now Pat. No. 6,685,920, which is a continuation-in-part of application No. 09/710,250, filed on Nov. 10, 2000, now Pat. No. 6,713,049.

(60) Provisional application No. 60/165,351, filed on Nov. 12, 1999.

(51) Int. Cl.
*A61K 7/16* (2006.01)

(52) U.S. Cl. .............................. 424/57; 424/49; 424/52; 433/215; 433/216

(58) Field of Classification Search ...................... None
See application file for complete search history.

(56) References Cited

U.S. PATENT DOCUMENTS

| | | | |
|---|---|---|---|
| 4,749,758 A | | 6/1988 | Dursch et al. |
| 4,877,603 A | * | 10/1989 | Degenhardt et al. .......... 424/57 |
| 5,011,913 A | | 4/1991 | Benedict et al. |
| 5,032,386 A | * | 7/1991 | Gaffar et al. ................. 424/49 |
| 5,049,375 A | | 9/1991 | Tsujita et al. |
| 5,130,146 A | | 7/1992 | Tsujita et al. |
| 5,296,214 A | | 3/1994 | Gaffar |
| 5,939,052 A | | 8/1999 | White, Jr. et al. |
| 5,980,776 A | | 11/1999 | Zakikhani et al. |
| 6,071,434 A | | 6/2000 | Davis et al. |
| 6,187,295 B1 | | 2/2001 | Glandorf |
| 6,190,644 B1 | | 2/2001 | McClanahan et al. |
| 6,350,436 B1 | | 2/2002 | Glandorf et al. |
| 6,555,094 B1 | | 4/2003 | Glandorf et al. |
| 2003/0165442 A1 | | 9/2003 | Baig et al. |

FOREIGN PATENT DOCUMENTS

| | | |
|---|---|---|
| GB | 1290724 | 9/1972 |
| JP | 62019506 | 1/1987 |

OTHER PUBLICATIONS

Derwent Abstract No. 1989-180073, "Oral care compsns., esp. for plaque and tartar control—contg. geminal di:phosphonic acid polymers", Degenhardt et al (1989).*

* cited by examiner

*Primary Examiner*—Gollamudi S. Kishore
*Assistant Examiner*—Snigdha Maewall
(74) *Attorney, Agent, or Firm*—Emelyn L. Hiland

(57) ABSTRACT

Disclosed are methods of enhancing fluoride incorporation into teeth and mineralization of teeth by use of oral care compositions comprising the combination of one or more fluoride ion sources and specialized phosphonate containing polymers or telomers. The present methods provide enhanced protection of teeth against caries and cavities and increased resistance to acid demineralization associated with caries processes as well as anticalculus (antitartar) benefits.

10 Claims, No Drawings

METHOD OF ENHANCING FLUORIDATION AND MINERALIZATION OF TEETH

CROSS-REFERENCE TO RELATED APPLICATIONS

This application is a continuation-in-part of U.S. application Ser. No. 10/319,108, filed Dec. 13, 2002 now U.S. Pat. No. 6,685,920, which is a continuation-in-part of U.S. application Ser. No. 09/710,250, filed Nov. 10, 2000 now U.S. Pat. No. 6,713,049, which claims the benefit of U.S Provisional Application No. 60/165351, filed Nov. 12, 1999, all herein incorporated by reference.

TECHNICAL FIELD

The present invention relates to methods of enhancing fluoride incorporation into teeth and/or mineralization of teeth by use of oral care compositions comprising the combination of one or more fluoride ion sources and specialized phosphonate containing polymers or telomers. The present methods provide enhanced protection of teeth against caries and cavities and increased resistance to acid demineralization associated with caries processes as well as anticalculus (antitartar) benefits.

BACKGROUND OF THE INVENTION

Oral care products such as toothpastes are routinely used by consumers as part of their oral care hygiene regimens. It is well known that oral care products can provide both therapeutic and cosmetic hygiene benefits to consumers. Therapeutic benefits include caries prevention which is typically delivered through the use of various fluoride salts; gingivitis prevention by the use of an antimicrobial agent such as triclosan, stannous fluoride, zinc citrate or essential oils; or hypersensitivity control through the use of ingredients such as strontium chloride or potassium nitrate. Cosmetic benefits provided by oral care products include the control of plaque and calculus formation, removal and prevention of tooth stain, tooth whitening, breath freshening, and overall improvements in mouth feel impression which can be broadly characterized as mouth feel aesthetics. For example, agents such as pyrophosphate salts have been used as antitartar agents and polymeric agents such as condensed phosphorylated polymers, polyphosphonates, and carboxylated polymers have been used in oral care compositions to provide benefits including tooth surface conditioning and control of tartar, staining and astringency. To illustrate further, commonly assigned U.S. Pat. No. 6,555,094 to Glandorf, et al. discloses oral care compositions comprising a stannous ion source, a fluoride ion source, and a polymeric mineral surface active agent that binds stannous, wherein the compositions provide effective antimicrobial activity for reducing plaque and gingivitis with minimal side effects of tooth staining and astringency. The compositions simultaneously provide reduction and control of supragingival calculus. Additional disclosures related to the use of polyphosphate as mineral surface active agent in oral care compositions include commonly assigned U.S. Pat. No. 5,939,052; U.S. Pat. No. 6,187,295; U.S. Pat. No. 6,350,436; and U.S. Pat. No. 6,190,644.

The present inventors have surprisingly discovered additional important benefits of oral care compositions comprising such polymeric agents that also have affinity for the tooth surface. These polymeric agents are believed to bind to the tooth surface or form compounds or complexes on the tooth surface, thereby forming a protective film or coating thereon. As a result of these protective coatings, tooth surfaces are provided with remarkable resistance and protection against erosion caused by the action of chemicals, such as harsh abrasives and acids, as disclosed in commonly assigned copending application U.S. Ser. No. 10/319,108 published as US 2003/0165442. Included among such polymeric agents are phosphonate containing structures, particularly those containing diphosphonate groups. Examples of suitable phosphonate containing polymers are disclosed in U.S. Pat. No. 5,011,913 to Benedict et al.; U.S. Pat. No. 4,877,603 to Degenhardt et al; U.S. Pat. No. 5,980,776 to Zakikhani et al; U.S. Pat. No. 6,071,434 to Davis et al; U.S. Pat. No. 5,296,214 to Gaffar, U.S. Pat. No. 4,749,758 to Dursch et al. and GB 1,290,724 assigned to Farbwerke Hoechst.

In addition to the anticalculus and antierosion benefits of these phosphonate containing polymers, the present inventors have discovered that oral care compositions containing these polymers in combination with a fluoride ion source provide surprisingly enhanced fluoride uptake and remineralization of teeth, thereby providing enhanced protection of teeth against caries and cavities and increased resistance to acid demineralization associated with caries processes. In particular, tooth surfaces and most particularly carious lesions treated with combinations of a fluoride ion source and phosphonate containing polymers show increased surface as well as internal acquisition of mineralized forms of calcium phosphate—acquired from supersaturated solutions—thus resulting in increased remineralization. Teeth treated with such combinations moreover exhibit increased resistance to demineralization and increases in fluoridation as a component of remineralized enamel.

The superior efficacy of combinations of polyphosphonates or phosphonate containing polymers with fluoride in promoting fluoridation, remineralization and providing acid resistance to the teeth is completely unexpected by known principles of phosphonate containing agents functioning as antitartar agents. These phosphonate ingredients, like other tartar control agents, are known to be effective in reducing (rather than increasing) the crystallization of mineral salts onto substrates in supersaturated solution. The localization of these materials on tooth surfaces can be expected to assist in tartar prevention and even do this without inhibiting remineralization processes below the tooth surface. However, the ability to modify the tooth surface to promote remineralization beneath the tooth surface such as in caries prevention is completely unexpected.

The tooth caries process is the result of calcium phosphate mineral loss from tooth substrate induced by localized plaque microbiological acid production from fermentable dietary substrates. If left uninhibited, the caries process results in sufficient mineral loss from teeth, which manifests as a loss of structural integrity and the formation of a cavity. (G. H. Nancollas, "*Kinetics of de- and remineralization,*" pp 113-128; A. Thylstrup, J. D. B. Featherstone and L. Fredebo, "*Surface morphology and dynamics of early enamel caries development,*" pp 165-184 in: *Demineralisation and Remineralisation of the Teeth*, IRL Press Ltd., (1983). S. A. Leach and W. M. Edgar, editors). The caries process is not continuous but is described by cyclic periods of mineral loss from teeth—particularly following ingestion of fermentable carbohydrates, followed by periods of no mineral loss or even mineral repair of damaged local regions. Remineralization refers to the process of repair of acid damaged tooth structure—by the recrystallization of mineral salts on the tooth architecture. Remineralization processes are a natural protective feature of saliva against the formation of tooth cavities, as saliva is supersaturated with respect to calcium phosphate tooth mineral salts. Remineralization is accelerated by fluoride ions in solution which increase local supersaturation with respect to fluoridated calcium phosphate deposition. Fluoridation refers to the acquisition of fluoride into tooth substrates resulting from topical treatments with fluoride agents. Often, but not always, remineralized teeth from treatments exhibit increases in fluoride uptake and retention. Demineralization is the process of mineral loss from teeth caused by plaque acids or dietary acids. Demineralization can occur on tooth surfaces or below tooth surfaces depending upon the composition of the acids, concentration and pH. Morevover the teeth with increased remineralization and fluoride uptake and retention also exhibit superior resistance to acid demineralization. The processes of fluoride incorporation into teeth, remineralization and resistance to demineralization represent primary mechanisms toward the reduction of tooth decay or other acid insults. The clinical relevance of the beneficial effects of these phosphonate containing polymer and fluoride combinations is that enhancements in fluoridation, remineralization and demineralization resistance match those of topical treatments, in particular elevated doses of fluorides, proven sufficient to provide clinical enhancements in caries prevention. (K. H. Lu et al.: "*A three year clinical comparison of a sodium monofluorophosphate dentifrice with sodium fluoride dentifrices on dental caries in children.*" *J Dent Child*. 1987;54:241-244) Benefits are further validated by improved resistance to cavity formation provided by these fluoride ion source/phosphonate polymer combinations in biological tests of anticaries efficacy such as those recommended in the FDA's *Final Caries Monograph* for OTC dentifrice products (specifically Test Method 37).

SUMMARY OF THE INVENTION

The present invention relates to a method of enhancing fluoride incorporation into and remineralization of a subject's teeth, by use of an oral care composition comprising a polymeric mineral surface-active agent containing phosphonate groups in combination with a fluoride ion source. The present method of treating teeth with such combination thus provides enhanced protection of teeth against caries (dental cavity formation) characterized by increased remineralization of teeth, increased fluoride deposition in teeth and increased resistance of teeth to acid demineralization while simultaneously providing anticalculus (antitartar) benefits.

These and other features, aspects, and advantages of the present invention will become evident to those skilled in the art from the detailed description which follows.

DETAILED DESCRIPTION OF THE INVENTION

While the specification concludes with claims which particularly point out and distinctly claim the invention, it is believed the present invention will be better understood from the following description.

All percentages and ratios used herein are by weight of the specific oral care composition and not of the overall oral care formulation that is delivered, unless otherwise specified. All measurements are made at 25° C., unless otherwise specified.

Herein, "comprising" means that other steps and other ingredients which do not affect the end result can be added. This term encompasses the terms "consisting of" and "consisting essentially of".

By "oral care composition" is meant a product which in the ordinary course of usage, is not intentionally swallowed for purposes of systemic administration of particular therapeutic agents, but is rather retained in the oral cavity for a time sufficient to contact substantially all of the dental surfaces and/or oral tissues for purposes of oral activity. The oral care composition of the present invention may be in the form of a toothpaste, dentifrice, tooth powder, topical oral gel, mouthrinse, denture product, mouthspray, lozenge, oral tablet, or chewing gum.

The term "dentifrice", as used herein, includes paste, gel, liquid or chewable (dentifrice) tablet formulations unless otherwise specified. The dentifrice composition may be a single phase composition or may be a combination of two or more dentifrice compositions. The dentifrice composition may be in any desired form, such as deep striped, surface striped, multilayered, having a gel surrounding a paste, or any combination thereof. Each dentifrice composition in a dentifrice comprising two or more separate dentifrice compositions may be contained in a physically separated compartment of a dispenser and dispensed side-by-side.

The term "dispenser", as used herein, means any pump, tube, or container suitable for dispensing the oral care compositions.

The term "teeth", as used herein, refers to natural teeth as well as artificial teeth or dental prosthesis.

The term "orally acceptable carrier" as used herein means any safe and effective materials for use in the compositions of the present invention. Such materials include fluoride ion sources; anticalculus agents; additional remineralizing agents such as calcium ion sources, phosphate ion sources and strontium ion sources; buffers; abrasive polishing materials; teeth whitening or bleaching agents such as peroxide sources; dentinal desensitizing agents; alkali metal bicarbonate salts; thickening materials; humectants; water; surfactants; titanium dioxide; flavor system; sweetening agents; xylitol; coloring agents and mixtures thereof.

The terms "mineralization" and "remineralization" are used interchangeably and refer to crystallization of mineral salts in the tooth architecture.

Herein, the terms "tartar" and "calculus" are used interchangeably and refer to mineralized dental plaque deposits.

The present invention relates to the use of oral care compositions comprising polymeric mineral surface active agents containing phosphonate groups in combination with one or more fluoride ion sources, to provide enhanced fluoridation or fluoride uptake and mineralization or remineralization of teeth thereby providing benefits of enhanced protection of teeth against caries and cavities and increased resistance to acid demineralization associated with caries processes as well as anticalculus or antitartar benefits.

The first essential component of the oral care composition of the present invention is a soluble fluoride source capable of providing free fluoride ions. The fluoride ion source may be formulated in the same phase as the phosphonate containing polymeric agent or may be in a separate phase from the phosphonate containing polymeric agent if necessary to aid in stability. Preferred soluble fluoride ion sources include sodium fluoride, stannous fluoride, indium fluoride, amine fluoride and sodium monofluorophosphate. Sodium fluoride and stannous fluoride are the most preferred soluble fluoride ion source. Stannous fluoride and methods of stabilization are described e.g., in U.S. Pat. No. 5,004,597 issued to Majeti et al. and in U.S. Pat. No. 5,578,293 issued to Prencipe et al Norris et al., U.S. Pat. No. 2,946,725, issued Jul. 26, 1960, and Widder et al., U.S. Pat. No. 3,678,154 issued Jul. 18, 1972, disclose additional fluoride ion sources.

The present compositions contain a soluble fluoride ion source capable of providing from about 50 ppm to about 5000 ppm, and preferably from about 250 ppm to about 3500 ppm of free fluoride ions.

The second essential component comprises one or more phosphonate containing polymeric mineral surface active agents which include any agent which in combination with a fluoride ion source will produce the desired fluoridation and mineralization effects. These phosphonate containing polymeric agents also provide desired surface conditioning effects including: 1) the effective desorption of portions of undesirable adsorbed pellicle proteins, in particular those associated with tooth stain binding, calculus development and attraction of undesirable microbial species; 2) creating a hydrophilic tooth surface immediately after treatment; and 3) maintaining surface conditioning effects and control of pellicle film for extended periods following product use, including post brushing and throughout more extended periods. The effect of creating an increased hydrophilic surface can be measured in terms of a relative decrease in water contact angles. The hydrophilic surface, importantly, is maintained on the tooth surface for an extended period after using the product, e.g., by tooth brushing. Many of these polymeric agents are also known or expected to provide tartar control or antistain/whitening or surface conditioning benefits when applied in oral care compositions, hence providing multiple clinical actions in improving the appearance of teeth, improving the tactile impression to consumers and maintaining the structure of the teeth.

Examples of suitable phosphonate containing polymeric mineral surface active agents include the diphosphonate-derivatized polymers in U.S. Pat. No. 5,011,913 to Benedict et al., such as diphosphonate modified polyacrylic acid; the geminal diphosphonate polymers disclosed as anticalculus agents in U.S. Pat. No. 4,877,603 to Degenhardt et al; phosphonate group containing copolymers disclosed in U.S. Pat. No. 4,749,758 to Dursch et al. and in GB 1,290,724 (both assigned to Hoechst) suitable for use in detergent and cleaning compositions; and the copolymers and cotelomers disclosed as useful for applications including scale and corrosion inhibition, coatings, cements and ion-exchange resins in U.S. Pat. No. 5,980,776 to Zakitchani et al. and U.S. Pat. No. 6,071,434 to Davis et al. Preferred polymers include the water-soluble copolymers of vinylphosphonic acid and acrylic acid and salts thereof disclosed in GB 1,290,724 wherein the copolymers contain from about 10% to about 90% by weight vinylphosphonic acid and from about 90% to about 10% by weight acrylic acid, more particularly wherein the copolymers have a weight ratio of vinylphosphonic acid to acrylic acid of 70% vinylphosphonic acid to 30% acrylic acid; 50% vinylphosphonic acid to 50% acrylic acid; or 30% vinylphosphonic acid to 70% acrylic acid. Other preferred polymers include the water soluble polymers disclosed by Zakikhani and Davis prepared by copolymerizing diphosphonate or polyphosphonate monomers having one or more unsaturated C=C bonds (e.g., vinylidene-1,1-diphosphonic acid and 2-(hydroxyphosphinyl)ethylidene-1,1-diphosphonic acid), with at least one further compound having unsaturated C=C bonds (e.g., acrylate and methacrylate monomers), such as those having the following structure:

1. Co-Telomer of Acrylic Acid and 2-(hydroxyphosphinyl) ethylidene-1,1-diphosphonic acid With Structure:

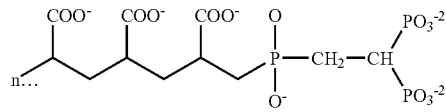

2. Co-Polymer of Acrylic Acid and Vinyldiphosphonic Acid With Structure:

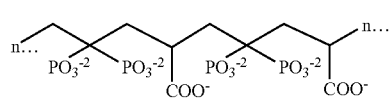

The preferred phosphonate containing polymeric mineral surface active agent will be stable with other components of the oral care composition such as ionic fluoride and metal ions and will not hydrolyze in high water content formulations, thus permitting a simple single phase dentifrice or mouthrinse formulation. If the polymeric mineral surface active agent does not have these stability properties, one option is a dual phase formulation with the polymeric mineral surface active agent separated from the fluoride or other incompatible component. Another option is to formulate a non-aqueous, essentially non-aqueous or limited water compositions to minimize reaction between the polymeric mineral surface active agent and other components or to allow formulation of polymeric mineral surface active agent in combination with agents that have limited aqueous stability or that are unstable in an aqueous environment.

Suitable polymers include the diphosphonate/acrylate polymers supplied by Rhodia under the designation ITC 1087 (Average MW 3000-60,000) and Polymer 1154 (Average MW 6000-55,000).

The amount of phosphonate containing polymeric mineral surface active agent required is an effective amount to provide the enhanced fluridation and mineralization benefits. An effective amount of phosphonate containing polymer will typically be from about 0.0001% to about 35%, preferably from about 0.1% to about 10%, more preferably from about 0.25% to about 2%, and most preferably from about 0.5% to about 1.5%, by weight of the total oral care composition.

In preparing the present compositions, it is desirable to add one or more aqueous carriers to the compositions. Such materials are well known in the art and are readily chosen by one skilled in the art based on the physical and aesthetic properties desired for the compositions being prepared. These carriers may be included at levels which do not interfere or prohibit the surface effects of the polymeric mineral surface active agent. The amount of polymeric mineral surface active agent may be increased to account for the additional carriers. Aqueous carriers typically comprise from about 50% to about 99%, preferably from about 70% to about 98%, and more preferably from about 80% to about 95%, by weight of the oral care composition.

The present compositions may contain a buffering agent. Buffering agents, as used herein, refer to agents that can be used to adjust the pH of the compositions to a range of about pH 4 to about pH 10. The oral care composition containing a polymeric mineral surface active agent will typically have a slurry pH of from about 4 to about 10, preferably from about 4.5 to about 8, and more preferably from about 5.5 to about 7. The buffering agents include alkali metal hydroxides, carbonates, sesquicarbonates, borates, silicates, phosphates, imidazole, and mixtures thereof. Specific buffering agents include monosodium phosphate, trisodium phosphate, sodium hydroxide, potassium hydroxide, alkali metal carbonate salts, sodium carbonate, imidazole, pyrophosphate salts, citric acid, and sodium citrate. Buffering agents are used at a level of from about 0.1% to about 30%, preferably from about 1% to about 10%, and more preferably from about 1.5% to about 3%, by weight of the present composition.

The present compositions may optionally contain anticalculus agents such as pyrophosphates and other polyphosphates. Pyrophosphates are among the best known for use in dental care products. Pyrophosphate salts may be used in the present invention as anticalculus agents or as buffering agents, as long as the remineralizing and fluoridating effects of the phosphonate containing polymeric surface active agent are not negatively affected. The pyrophosphate salts useful in the present compositions include the dialkali metal pyrophosphate salts, tetra alkali metal pyrophosphate salts, and mixtures thereof. Disodium dihydrogen pyrophosphate ($Na_2H_2P_2O_7$), tetrasodium pyrophosphate ($Na_4P_2O_7$), and tetrapotassium pyrophosphate ($K_4P_2O_7$) in their unhydrated as well as hydrated forms are the preferred species. In compositions of the present invention, the pyrophosphate salt may be present in one of three ways: predominately dissolved, predominately undissolved, or a mixture of dissolved and undissolved pyrophosphate.

Compositions comprising predominately dissolved pyrophosphate refer to compositions where at least one pyrophosphate ion source is in an amount sufficient to provide at least about 1.0% free pyrophosphate ions. The amount of free pyrophosphate ions may be from about 1% to about 15%, preferably from about 1.5% to about 10%, and most preferably from about 2% to about 6%, by weight of the composition. Free pyrophosphate ions may be present in a variety of protonated states depending on the pH of the composition.

Compositions comprising predominately undissolved pyrophosphate refer to compositions containing no more than about 20% of the total pyrophosphate salt dissolved in the composition, preferably less than about 10% of the total pyrophosphate dissolved in the composition. Tetrasodium pyrophosphate salt is the preferred pyrophosphate salt in these compositions. Tetrasodium pyrophosphate may be the anhydrous salt form or the decahydrate form, or any other species stable in solid form in the dentifrice compositions. The salt is in its solid particle form, which may be its crystalline and/or amorphous state, with the particle size of the salt preferably being small enough to be aesthetically acceptable and readily soluble during use. The amount of pyrophosphate salt useful in making these compositions is any tartar control effective amount, and is generally from about 1.5% to about 15%, preferably from about 2% to about 10%, and most preferably from about 2.5% to about 8%, by weight of the composition. Some or all of the tetrasodium pyrophosphate may be undissolved in the product and present as tetrasodium pyrophosphate particles. Pyrophosphate ions in different protonated states (e.g., $HP_2O_7^{-3}$) may also exist depending upon the pH of the composition and if part of the tetrasodium pyrophosphate is dissolved.

Compositions may also comprise a mixture of dissolved and undissolved pyrophosphate salts. Any of the above mentioned pyrophosphate salts may be used.

The inorganic polyphosphate salts desired include tripolyphosphate, tetrapolyphosphate and hexametaphosphate, among others. Polyphosphates larger than tetrapolyphosphate usually occur as amorphous glassy materials. Preferred in this invention are the linear "glassy" polyphosphates having the formula:

wherein X is sodium or potassium and n averages from about 6 to about 125. Preferred are polyphosphates manufactured by FMC Corporation which are commercially known as Sodaphos (n≈6), Hexaphos (n≈13), and Glass H (n≈21). These polyphosphates may be used alone or in an combination thereof.

The phosphate sources are described in more detail in Kirk & Othmer, *Encyclopedia of Chemical Technology*, Fourth Edition, Volume 18, Wiley-Interscience Publishers (1996).

Additional anticalculus agents that may be used in place of or in combination with the phosphate salt include such known materials as synthetic anionic polymers including polyacrylates and copolymers of maleic anhydride or acid and methyl vinyl ether (e.g., Gantrez), as described, for example, in U.S. Pat. No. 4,627,977, to Gaffar et al.; as well as, e.g., polyamino propane sulfonic acid (AMPS), zinc citrate trihydrate, diphosphonates (e.g., EHDP; AHP), polypeptides (such as polyaspartic and polyglutamic acids), and mixtures thereof.

An abrasive polishing material may also be included in the oral care compositions. The abrasive polishing material contemplated for use in the compositions of the present invention can be any material which does not excessively abrade dentin. The abrasive polishing material should be formulated in the care composition so that it does not compromise the stability of any ingredients, in particular the fluoride ion source and the polyphosphonate containing polymeric agent. Typical abrasive polishing materials include silica gels and precipitates; aluminas; phosphates including orthophosphates, polymetaphosphates, and pyrophosphates; and mixtures thereof. Specific examples include dicalcium orthophosphate dihydrate, calcium pyrophosphate, tricalcium phosphate, calcium polymetaphosphate, insoluble sodium polymetaphosphate, hydrated alumina, beta calcium pyrophosphate, calcium carbonate, and resinous abrasive materials such as particulate condensation products of urea and formaldehyde, and others such as disclosed by Cooley et al in U.S. Pat. No. 3,070,510, issued Dec. 25, 1962. Mixtures of abrasives may also be used.

Silica dental abrasives of various types are preferred because of their unique benefits of exceptional dental cleaning and polishing performance without unduly abrading tooth enamel or dentine. The silica abrasive polishing materials herein, as well as other abrasives, generally have an average particle size ranging between about 0.1 to about 30 microns, and preferably from about 5 to about 15 microns. The abrasive can be precipitated silica or silica gels such as the silica xerogels described in Pader et al., U.S. Pat. No. 3,538,230, issued Mar. 2, 1970, and DiGiulio, U.S. Pat. No. 3,862,307, issued Jan. 21, 1975. Preferred are the silica xerogels marketed under the trade name "Syloid" by the W.R. Grace & Company, Davison Chemical Division. Also preferred are the precipitated silica materials such as those marketed by the J. M. Huber Corporation under the trade name, "Zeodent", particularly the silica carrying the designation "Zeodent 118", "Zeodent 119" and "Zeodent 109". The types of silica dental abrasives useful in the toothpastes of the present invention are described in more detail in Wason, U.S. Pat. No. 4,340,583, issued Jul. 29, 1982. Silica abrasives are also described in Rice, U.S. Pat. Nos. 5,589,160; 5,603,920; 5,651,958; 5,658,553; and 5,716,601. Also useful are silica abrasives described commercially as Sorbosil AC 33, AC 35, AC 39 and AC 77 supplied by Ineos. The abrasive in the toothpaste compositions described herein is generally present at a level of from about 6% to about 70% by weight of the composition. Preferably, toothpastes contain from about 10% to about 50% of abrasive, by weight of the dentifrice composition.

The present invention may include a teeth whitening or bleaching agent in the oral care composition. The actives suitable for whitening are selected from the group consisting of peroxides, metal chlorites, perborates, percarbonates, peroxyacids, persulfates, and combinations thereof. Suitable peroxide compounds include hydrogen peroxide, urea peroxide, calcium peroxide, carbamide peroxide, and mixtures thereof. A preferred peroxide source is calcium peroxide. Suitable metal chlorites include calcium chlorite, barium chlorite, magnesium chlorite, lithium chlorite, sodium chlorite, and potassium chlorite. Additional whitening actives may be hypochlorite and chlorine dioxide. A preferred chlorite is sodium chlorite. A preferred percarbonate is sodium percarbonate. Preferred persulfates are oxones. The present composition may contain from about 0.01% to about 10%, preferably from about 0.1% to about 5%, more preferably from about 0.2% to about 3%, and most preferably from about 0.3% to about 0.8% of a teeth whitening active, by weight of the dentifrice composition.

The present invention may also include an alkali metal bicarbonate salt. Alkali metal bicarbonate salts are soluble in water and unless stabilized, tend to release carbon dioxide in an aqueous system. Sodium bicarbonate, also known as baking soda, is the preferred alkali metal bicarbonate salt. The alkali metal bicarbonate salt also functions as a buffering agent. The present composition may contain from about 0.5% to about 70%, preferably from about 0.5% to about 30%, more preferably from about 2% to about 20%, and most preferably from about 5% to about 18% of an alkali metal bicarbonate salt, by weight of the dentifrice composition.

Another optional component of the present compositions is a dentinal desensitizing agent to control hypersensitivity, such as salts of potassium, calcium, strontium and tin including nitrate, chloride, fluoride, phosphates, pyrophosphate, polyphosphate, citrate, oxalate and sulfate.

The present invention provides compositions in the form of toothpastes, dentifrices, tooth powder, topical oral gels, mouthrinses, denture product, mouthsprays, lozenges, chewable oral tablets, and chewing gums. Typically these compositions will contain some thickening material or binders to provide a desirable consistency. Preferred thickening agents are carboxyvinyl polymers, carrageenan, hydroxyethyl cellulose, and water soluble salts of cellulose ethers such as sodium carboxymethylcellulose and sodium hydroxyethyl cellulose. Natural gums such as gum karaya, xanthan gum, gum arabic, and gum tragacanth can also be used. Colloidal magnesium aluminum silicate or finely divided silica can be used as part of the thickening agent to further improve texture. Thickening agents can be used in an of amount from about 0.1% to about 15%, by weight of the dentifrice composition.

Another optional component of the compositions desired herein is a humectant. The humectant serves to keep toothpaste compositions from hardening upon exposure to air and certain humectants can also impart desirable sweetness of flavor to toothpaste compositions. Suitable humectants for use in the invention include glycerin, sorbitol, polyethylene glycol, propylene glycol, and other edible polyhydric alcohols. The humectant generally comprises from about 0% to 70%, and preferably from about 15% to 55%, by weight of the composition.

Water employed in the preparation of commercially suitable oral care compositions should preferably be of low ion content and free of organic impurities. Water will generally comprise from about 0% to about 70%, and preferably from about 5% to about 50%, by weight of the composition herein. The total amount of water includes the added water plus that which is introduced with other materials, such as with sorbitol, silca, surfactant solutions and color solutions.

The present compositions may also comprise surfactants, also commonly referred to as sudsing agents. Suitable surfactants are those which are reasonably stable and foam throughout a wide pH range. The surfactant may be anionic, nonionic, amphoteric, zwitterionic, cationic, or mixtures thereof. Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate and sodium coconut monoglyceride sulfonates are examples of anionic surfactants of this type. Other suitable anionic surfactants are sarcosinates, such as sodium lauroyl sarcosinate, taurates, sodium lauryl sulfoacetate, sodium lauroyl isethionate, sodium laureth carboxylate, and sodium dodecyl benzenesulfonate. Mixtures of anionic surfactants can also be employed. Many suitable anionic surfactants are disclosed by Agricola et al., U.S. Pat. No. 3,959,458, issued May 25, 1976. Nonionic surfactants which can be used in the compositions of the present invention can be broadly defined as compounds produced by the condensation of alkylene oxide groups (hydrophilic in nature) with an organic hydrophobic compound which may be aliphatic or alkyl-aromatic in nature. Examples of suitable nonionic surfactants include poloxamers (sold under trade name Pluronic), polyoxyethylene, polyoxyethylene sorbitan esters (sold under trade name Tweens), fatty alcohol ethoxylates, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides, and mixtures of such materials. The amphoteric surfactants useful in the present invention can be broadly described as derivatives of aliphatic secondary and tertiary amines in which the aliphatic radical can be a straight chain or branched and wherein one of the aliphatic substituents contains from about 8 to about 18 carbon atoms and one contains an anionic water-solubilizing group, e.g., carboxylate, sulfonate, sulfate, phosphate, or phosphonate. Other suitable amphoteric surfactants are betaines, specifically cocamidopropyl betaine. Mixtures of amphoteric surfactants can also be employed. Many of these suitable nonionic and amphoteric surfactants are disclosed by Gieske et al., U.S. Pat. No. 4,051,234, issued Sep. 27, 1977. The present composition typically comprises one or more surfactants each at a level of from about 0.25% to about 12%, preferably from about 0.5% to about 8%, and most preferably from about 1% to about 6%, by weight of the composition.

Titanium dioxide may also be added to the present composition. Titanium dioxide is a white powder which adds opacity to the compositions. Titanium dioxide generally comprises from about 0.25% to about 5%, by weight of the composition.

Coloring agents may also be added to the present composition. The coloring agent may be in the form of an aqueous solution, preferably 1% coloring agent in a solution of water. Color solutions generally comprise from about 0.01% to about 5%, by weight of the composition.

A flavor system can also be added to the compositions. Suitable flavoring components include oil of wintergreen, oil of peppermint, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, ethyl vanillin, heliotropine, 4-cis-heptenal, diacetyl, methyl-para-tert-butyl phenyl acetate, and mixtures thereof. Coolants may also be part of the flavor system. Preferred coolants in the present compositions are the para-menthan carboxyamide agents such as N-ethyl-p-menthan-3-carboxamide (known commercially as "WS-3") and mixtures thereof. A flavor system is generally used in the compositions at levels of from about 0.001% to about 5%, by weight of the composition.

The present invention may also include xylitol. Xylitol is a sugar alcohol that is used as a sweetener and humectant. Xylitol may provide a therapeutic effect, such as an antibacterial or anticaries effect. The present compositions typically comprise xylitol at a level from about 0.01% to about 25%, preferably from about 3% to about 15%, more preferably from about 5% to about 12%, and most preferably from about 9% to about 11%, by weight of the total composition. Alternatively, if xylitol is used as a sweetener, it may be present at a lower level, such as from about 0.005% to about 5%, by weight of the dentifrice composition.

Sweetening agents can be added to the compositions. These include saccharin, dextrose, sucrose, lactose, maltose, levulose, aspartame, sodium cyclamate, D-tryptophan, dihydrochalcones, acesulfame, and mixtures thereof. Various coloring agents may also be incorporated in the present invention. Sweetening agents and coloring agents are generally used in toothpastes at levels of from about 0.005% to about 5%, by weight of the composition.

The present invention may also include other agents, such as antimicrobial agents. Included among such agents are water insoluble non-cationic antimicrobial agents such as halogenated diphenyl ethers, phenolic compounds including phenol and its homologs, mono and poly-alkyl and aromatic halophenols, resorcinol and its derivatives, bisphenolic compounds and halogenated salicylanilides, benzoic esters, and halogenated carbanilides. The water soluble antimicrobials include quaternary ammonium salts and bis-biquanide salts, among others. Triclosan monophosphate is an additional water soluble antimicrobial agent. The quaternary ammonium agents include those in which one or two of the substitutes on the quaternary nitrogen has a carbon chain length (typically alkyl group) from about 8 to about 20, typically from about 10 to about 18 carbon atoms while the remaining substitutes (typically alkyl or benzyl group) have a lower number of carbon atoms, such as from about 1 to about 7 carbon atoms, typically methyl or ethyl groups. Dodecyl trimethyl ammonium bromide, tetradecylpyridinium chloride, domiphen bromide, N-tetradecyl-4-ethyl pyridinium chloride, dodecyl dimethyl (2-phenoxyethyl) ammonium bromide, benzyl dimethylstearyl ammonium chloride, cetyl pyridinium chloride, quaternized 5-amino-1,3-bis(2-ethyl-hexyl)-5-methyl hexa hydropyrimidine, benzalkonium chloride, benzethonium chloride and methyl benzethonium chloride are exemplary of typical quaternary ammonium antibacterial agents. Other compounds are bis [4-(R-amino)-1-pyridinium] alkanes as disclosed in U.S. Pat. No. 4,206,215, issued Jun. 3, 1980, to Bailey. Other antimicrobials such as copper bisglycinate, copper glysinate, zinc citrate, and zinc lactate may also be included. Also useful are enzymes, including endoglycosidase, papain, dextranase, mutanase, and mixtures thereof. Such agents are disclosed in U.S. Pat. No. 2,946,725, Jul. 26, 1960, to Norris et al. and in U.S. Pat. No. 4,051,234, Sep. 27, 1977 to Gieske et al. Specific antimicrobial agents include chlorhexidine, triclosan, triclosan monophosphate, and flavor oils such as thymol. Triclosan and other agents of this type are disclosed in Parran, Jr. et al., U.S. Pat. No. 5,015,466, issued May 14, 1991, and U.S. Pat. No. 4,894,220, Jan. 16, 1990 to Nabi et al. These agents may be present at levels of from about 0.01% to about 1.5%, by weight of the dentifrice composition.

The oral care compositions of the present invention may be in the form of toothpastes, dentifrices, topical oral gels, mouthrinses, denture products, mouthsprays, lozenges, oral tablets, or chewing gums. The dentifrice compositions may be a paste, gel, liquid, chewable tablet or any configuration or combination thereof. If a dual phase formulation is used, it is preferred that the dentifrice compositions be physically separated. Also for aesthetics reasons, it is preferred that in dual phase compositions, one composition be a paste and the other composition be a gel. The dispenser may be a tube, pump, or any other container suitable for dispensing toothpaste. Dual compartment packages suitable for this purpose are described in U.S. Pat. No. 4,528,180, issued Jul. 9, 1985; U.S. Pat. No. 4,687,663, issued Aug. 18, 1987; and 4,849,213, issued Jul. 18, 1989, all to Shaeffer. The dispenser will deliver approximately equal amounts of each dentifrice composition through an opening. The compositions may intermix once dispensed. Alternatively, the oral care formulation may be delivered from a kit containing two separate dispensers which are used to deliver two dentifrice compositions that are both used simultaneously.

The method of use for providing enhanced fluoridation and remineralization herein comprises contacting a subject's dental enamel surfaces and mucosa in the mouth with the oral care compositions according to the present invention. The method of use may be by brushing with a dentifrice or rinsing with a dentifrice slurry or mouthrinse. Other methods include contacting the topical oral gel, dentures product, mouthspray, or other form with the subject's teeth and oral mucosa. The subject may be any person or lower animal whose tooth surfaces contact the oral care composition. The present methods are particularly advantageous for subjects in need of increased fluoridation and/or remineralization such as subjects having carious lesions that lead to cavities.

It should be understood that the present invention relates not only to methods for delivering the present compositions comprising a fluoride ion source and phosphonate containing polymeric agent to the oral cavity of a human, but also to methods of delivering these compositions to the oral cavity of other animals, e.g., household pets or other domestic animals, or animals kept in captivity.

For example, a method of use may include a person brushing a dog's teeth with one of the present dentifrice compositions. Another example would include the rinsing of a cat's mouth with an oral care composition for a sufficient amount of time to see a benefit. Pet care products such as specially engineered foods, biscuits, chews and toys may be formulated to contain the present oral care compositions.

For example, the composition comprising the phosphonate polymeric surface active agent and fluoride source may be incorporated into a relatively supple but strong and durable material such as rawhide, ropes made from natural or synthetic fibers, and polymeric articles made from nylon, polyester or thermoplastic polyurethane. As the animal chews, licks or gnaws the product, the incorporated active elements are released into the animal's oral cavity into a salivary medium, comparable to an effective brushing or rinsing.

EXAMPLES

The following examples further describe and demonstrate embodiments within the scope of the present invention. These examples are given solely for the purpose of illustration and are not to be construed as limitations of the present invention as many variations thereof are possible without departing from the spirit and scope.

Example I

In order to assess caries protection potential of the present compositions, a pH cycling model was used to compare the effectiveness of a phosphonate polymer+fluoride toothpaste compared to a comparable fluoride toothpaste that did not contain phosphonate polymer. The protocol used is essentially equivalent to the method described in R. V. Faller, et al. "*The comparative anticaries efficacy of Crest toothpaste relative to some marketed Chinese toothpastes—results of in vitro pH cycling testing,*". *Int Dent J*. 1997, 47: 313-320.

In this test, discs of enamel are removed from extracted human teeth. The naturally fluoride-rich surface is removed via grinding and polishing, presenting a human enamel surface essentially free of background fluoride. Each specimen is exposed to buffered acid solutions, effecting the development of lesions that are similar to naturally occurring caries lesions. Groups of specimens are treated in human saliva, exposed for short periods to mixtures of test product/pooled human saliva, cycles of daily acid challenge, and cycles of daily saliva exposure. Upon completion of treatments, each specimen is sampled to determine the level of fluoride incorporated into each tooth (measured as μg F/cm$^2$ as shown in Tables 1 and 4), as fluoride incorporation has been positively correlated with caries clinical performance of various toothpaste formulations (N. Y. Sakkab et al. "*Fluoride in deciduous teeth from an anti-caries clinical study,*". *J Dent Res*.,1984; 63:1201-1205). A portion of the surface of each specimen is then covered with a protective coating, and the remaining portion of the surface exposed to an acid challenge for a specified period of time to determine the acid resistance of this product treated area. Thin cross-sections are removed from each specimen, and each specimen is assessed via quantitative transverse microradiography to determine the level of remineralization that occurred [vs. control measured as delta Z ($\Delta Z$) as shown in Table 2, which is a quantitative measure of the difference in mineral content of the enamel, comparing demineralized-then-treated areas of the specimen to an area of the same specimen that was initially demineralized but not exposed to the test product] and the level of resistance to a secondary acid challenge [vs. control measured again as delta Z ($\Delta Z$) as shown in Table 3, in this case being the difference in mineral content of the demineralized—then treated—then acid challenged areas of the specimen compared to an area of the same specimen that was initially demineralized but not exposed to the test product]. [D. J. White (1987) "*Reactivity of fluoride dentifrices with artificial caries. 1. Effects on early carious lesions: F uptake, surface hardening and remineralization.*" *Caries Res*. 22: 27-36); R. V. Faller (1995) "*The application of in situ models for evaluation of new fluoride containing systems,*" *Adv. Dent. Res*. 9(3): 290-299] In measuring remineralization and acid resistance, the initial starting point is an enamel specimen that has been exposed to an acid environment, initiating an early stage of cavity formation, or lesion area. Remineralization values are routinely reported as negative in value, as they represent a reversal of the initial, starting value for lesion area. Thus, the more negative, the better. The same methods are used to report acid resistance values, with the more negative numbers (compared to control) representing more effective product performance in these model systems. The results of this study demonstrated enhanced deposition of fluoride into the demineralized enamel specimens from the fluoride+phosphonate polymer containing toothpaste—relative to the control paste containing fluoride but no phosphonate polymer as shown in Tables 1 and 4. Further, enhancement in both remineralization and resistance to a secondary acid challenge were demonstrated for the phosphonate polymer+fluoride containing toothpaste vs. the fluoride control as shown in Tables 2 and 3, respectively.

TABLE 1

Fluoride Uptake

| Treatment | μg F/cm$^2$ |
|---|---|
| 2800 ppm F | 44.054 |
| 1100 ppm F + 2.5% Polymer 1154 | 38.425 |
| 1100 ppm F + 5.0% ITC 1087 | 32.354 |
| 1100 ppm F + 2.5% ITC 1087 | 24.552 |
| 1100 ppm F | 22.584 |
| 250 ppm F | 7.042 |
| 0 ppm | 3.095 |

TABLE 2

Remineralization

| Treatment | $\Delta Z$ |
|---|---|
| 1100 ppm F + 2.5% Polymer 1154 | −765.167 |
| 2800 ppm F | −750.567 |
| 1100 ppm F + 5.0% ITC 1087 | −713.750 |
| 1100 ppm F + 2.5% ITC 1087 | −706.400 |
| 1100 ppm F | −481.950 |
| 250 ppm F | −179.775 |
| 0 ppm F | 3.400 |

TABLE 3

Acid Resistance

| Treatment | $\Delta Z$ |
|---|---|
| 1100 ppm F + 2.5% ITC 1087 | −389.400 |
| 2800 ppm F | −387.800 |
| 1100 ppm F + 5.0% ITC 1087 | −183.250 |
| 1100 ppm F + 2.5% Polymer 1154 | −168.467 |
| 1100 ppm F | −106.650 |
| 250 ppm F | 1164.375 |
| 0 ppm F | 1639.300 |

TABLE 4

Fluoride Uptake

| Treatment | (μg/cm$^2$) |
|---|---|
| 2.5% ITC 1087 + 1100 ppm F | 28.316 |
| 2.5% Polymer 1154 + 1100 ppm F | 25.817 |
| 1.6% ITC 1087 + 1100 ppm F | 25.289 |
| 1100 ppm F | 18.980 |
| 0 ppm F | −1.040 |

Example II

Dentifrice Formulations

| Ingredient | Formula A | Formula B | Formula C | Formula D | Formula E |
|---|---|---|---|---|---|
| Sorbitol (70%) | 58.74 | 59.46 | 58.74 | 40.00 | — |
| Silica | 20.00 | 20.00 | 20.00 | 20.00 | 25.00 |
| Purified Water | 8.961 | 10.06 | 8.076 | 15.94 | — |
| Sodium Lauryl Sulfate (28%) | 4.000 | 4.000 | 4.000 | 4.000 | 2.500 |
| Poly (diphosphonate/acrylate) (25%) | 3.636 | 1.818 | 3.636 | 10.00 | 10.00 |
| Disodium Phosphate | 1.450 | 1.450 | 1.450 | — | — |
| Flavor | 0.900 | 0.900 | 0.900 | 1.500 | 0.800 |
| Monosodium phosphate | 0.590 | 0.590 | 0.590 | — | — |
| Trisodium Phosphate | — | — | — | — | 1.100 |
| Titanium Dioxide | 0.525 | 0.525 | 0.525 | — | — |
| Xanthan Gum | 0.475 | 0.475 | 0.475 | — | 0.600 |
| Carbopol | 0.300 | 0.300 | 0.300 | — | — |
| Hydroxyethyl Cellulose | — | — | — | 0.500 | — |
| Carageenan | — | — | — | 0.800 | 0.600 |
| Sodium Hydroxide | — | — | — | 0.400 | — |
| Sodium Saccharin | 0.130 | 0.130 | 0.130 | 0.455 | 0.500 |
| Glycerin | — | — | — | — | 38.52 |
| Poloxamer | — | — | — | 5.000 | — |
| Polyethylene Glycol | — | — | — | — | 7.00 |
| Propylene Glycol | — | — | — | — | 7.00 |
| FD&C Blue # 1 | 0.050 | 0.050 | 0.050 | 0.300 | 0.300 |
| Sodium Fluoride | 0.243 | 0.243 | — | — | — |
| Stannous Fluoride | — | — | — | 0.454 | 0.454 |
| Sodium Monofluorophosphate | — | — | 1.128 | — | — |
| Stannous Chloride | — | — | — | 0.653 | 0.653 |

Add the glycerin or sorbitol solution, water and color solution to a mixing vessel. Begin heating to approximately 50° C. Add the fluoride salt, sodium saccharin, and other salts (e.g., monosodium phosphate, trisodium phosphate) to the solution. Disperse the binders/thickeners as well as the titanium dioxide into the silica using a separate container. Add the binder/thickener blend to the glycerin/sorbitol/salt mixture in the mix tank. Mix until binders are well hydrated and the silica is uniformly dispersed. Mixing under vacuum during binder hydration will reduce entrapped air. After the binder hydration step, begin cooling the batch. When the temperature reaches about 40° C. add the sodium alkyl sulfate solution, flavor and phosphonate polymer solution. Continue to mix the batch for at least 3 minutes. Finally deaerate the batch to achieve the target specific gravity.

All documents cited are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

We claim:

1. A method of enhancing protection of teeth against caries and cavities and increasing resistance to acid demineralization associated with caries processes comprising administering to a subject's oral cavity an oral care composition comprising a combination of (a) a phosphonate group containing copolymer or cotelomer that is substantive to teeth and provides increased hydrophilic character to teeth surfaces and (b) one or more fluoride ion sources to provide enhanced fluoride incorporation into and remineralization of the subject's teeth, wherein the phosphonate group containing copolymer or cotelomer has an average molecular weight of from about 3,000 to about 60,000 and is prepared by copolymerizing a phosphonate containing monomer selected from vinyldiphosphonic acid, vinylidene-1,1-diphosphonic acid, 2-(hydroxyphosphinyl)ethylidene-1,1-diphosphonic acid) or salts thereof with at least one other monomer selected from acrylic acid, methacrylic acid or salts thereof.

2. A method according to claim 1, wherein the phosphonate group containing copolymer or cotelomer comprised in the oral care composition are selected from acrylic acid/2-(hydroxyphosphinyl)ethylidene-1,1-diphosphonic acid cotelomer, acrylic acid/vinyldiphosphonic acid copolymer or salts thereof.

3. A method according to claim 2, wherein the phosphonate group containing copolymer or cotelomer comprised in the oral care composition is poly (vinyldiphosphonate/acrylate).

4. A method according to claim 1, wherein the fluoride ion source is selected from sodium fluoride, stannous fluoride, indium fluoride, amine fluoride and sodium monofluorophosphate and provides from about 50 ppm to about 5000 ppm of free fluoride ions.

5. A method according to claim 1, wherein the administered oral care composition further comprises one or more additional oral care agents selected from the group consisting of antimicrobial/antiplaque agents, biofilm inhibiting agents, dentinal desensitizing agents; anticalculus agents, calcium ion sources, strontium ion sources, phosphate ion sources, teeth whitening agents, odor masking agents; and mixtures thereof.

6. A method according to claim 5, wherein the administered oral care composition further comprises an antimicrobial/antiplaque agent selected from the group consisting of triclosan, cetylpyridinium chloride, chlorhexidine, alexidine, hexetidine, sanguinarine, benzalkonium chloride, salicylanilide, domiphen bromide, cetylpyridinium chloride (CPC), tetradecylpyridinium chloride (TPC), N-tetradecyl-4-ethylpyridinium chloride (TDEPC), octenidine, delmopinol, octapinol, nisin, a zinc ion source, a stannous ion source, a copper ion source, an essential oil and mixtures thereof, thereby providing benefits against gingivitis, periodontal disease and oral infections.

7. A method according to claim 5, wherein the administered oral care composition further comprises one or a mixture of dentinal desensitizing agent selected from salts of potassium, calcium, sirontium and tin.

8. A method according to claim 5, wherein the administered oral care composition further comprises one or a mixture of a calcium ion source, a phosphate ion source or a strontium ion source, thereby further enhancing remineralization of teeth.

9. A method according to claim 5, wherein the administered oral care composition further comprises a teeth whitening agent selected from the group consisting of hydrogen peroxide, calcium peroxide, urea peroxide, sodium percarbonate, sodium chlorite and mixtures thereof.

10. A method according to claim 1, wherein the administered oral care composition is in a form selected from toothpaste, tooth powder, tooth gel, mouthrinse, denture product, mouthspray, lozenge, chewable dentifrice tablet, or chewing gum.

* * * * *